US00PP14222P29

(12) United States Plant Patent
Morrison

(10) Patent No.: US PP14,222 P2
(45) Date of Patent: Oct. 14, 2003

(54) **ORNAMENTAL WINTER *HIBISCUS MOSCHEUTOS* NAMED 'MORRISON-GILBERG (VI)'**

(50) Latin Name: *Hibiscus moscheutos*
Varietal Denomination: 'Morrison-Gilberg (VI)'

(75) Inventor: William L. Morrison, Park Ridge, IL (US)

(73) Assignee: Gilberg Perennial Farms, Inc., Glencoe, MO (US)

( * ) Notice: Subject to any disclaimer, the term of this patent is extended or adjusted under 35 U.S.C. 154(b) by 0 days.

(21) Appl. No.: 09/528,909

(22) Filed: Mar. 20, 2000

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—Anne Marie Grünberg

(57) ABSTRACT

A new and distinct hybrid variety *Hibiscus moscheutos* cultivar, particularly distinguished by having flowers of from ten to twelve inches in diameter that are mostly white, with a pale tinge of pink (Red-Purple Group 69B) on the margins and a deep red eye (Red Group 45A). The length of the blooming cycle is about four to five weeks. The flowers, which have completely overlapping petals, retain their flat shape for two full days, except when temperatures are exceptionally warm. Distinguishing characteristics are constant and stable in asexually reproduced plants.

3 Drawing Sheets

BACKGROUND OF THE INVENTION

The present invention relates to a new and distinct variety of herbaceous perennial, more particularly to a hybrid variety of hibiscus.

BRIEF SUMMARY OF THE INVENTION

The new cultivar was developed by William L. Morrison as a progeny by cross-pollination in a garden in Park Ridge, Ill., a suburb of Chicago. The plant was originally produced as a seedling and has been successfully asexually reproduced by root crown division in a greenhouse located in the backyard of William Morrison, 1023 West Crescent Avenue, Park Ridge, Ill. 60068. The plant has also been reproduced by vegetative reproduction, i.e., by tip and stem cuttings. The original seedling had parentage of 'Kilimanjaro' (patent applied for concurrently herewith) pollen parent and 'Very White' (unpatented) seed parent, both of which are cultivars of *Hibiscus moscheutos* grown and named by William L. Morrison. The present cultivar is a herbaceous perennial; the stalks die back to ground level every winter and new stalks emerge in late spring. The trade name "MT. BLANC" has been coined for this cultivar, although the cultivar was neither marketed nor was its existence made public prior to the filing of the present plant patent application.

The present cultivar is distinguished by having flowers of from ten to twelve inches in diameter. These unusually large flowers can be cut and used for centerpiece displays. By comparison, *Hibiscus rosa-sinensis* (Chinese Hibiscus Rose of China) flowers are two to six inches in diameter, and *Hibiscus syriacus* (Rose-of-Sharon or Althea) flowers are three to six inches in diameter.

The flowers of the present cultivar may be distinguished from those of its seed parent in that they are larger by 4–5 inches, they are tinged with pink, and they last 1–2 days longer. The flowers differ from those of its pollen parent in that they are mostly white, instead of red. The present cultivar has longer laterals and a 1–2 week longer blooming cycle than 'Very White'. Another important difference is that the flowers of the present cultivar retain their flat shape for 2–3 days.

The greatest number of flowers for the present cultivar was obtained in environments of half to full sun. The largest flowers were obtained at summer temperatures from 70 to 100 degrees Fahrenheit. Smaller flowers were observed to bloom at temperatures as low as 50 to 60 degrees Fahrenheit.

Reproduction by root crown division consistently produces plants with identical, stable characteristics. A further botanical description of the new variety follows below. In the following descriptions, color references are made to The R.H.S. Colour Chart (1995, The Royal Horticultural Society), except where general terms of ordinary significance are used. Distinguishing color characteristics are listed on the attached Plant Color Coding Sheet. The distinguishing characteristics listed thereon should not necessarily be assumed to be exhaustive. Although the listed characteristics are believed to be the primary distinguishing color characteristics of the cultivar, it is possible that others may become evident upon further observation and comparison with other cultivars. These descriptions were made from specimens reproduced and grown under greenhouse and outdoor gardening conditions in suburban St. Louis, Mo.

BRIEF DESCRIPTION OF THE DRAWINGS

The accompanying drawings clearly depicts the new variety, showing the colors as true as it is reasonably possible to obtain in a colored reproduction of this type. Actual flower, leaf, sepal, and bud colors may differ from flower, leaf, sepal, and bud colors in the photograph due to light reflectance.

The drawings labeled "FIG. 1" and "FIG. 2" are close-up views of freshly cut portions of the *Hibiscus moscheutos* named 'Morrison-Gilberg (VI)' cultivar of the present invention.

Figure 1:
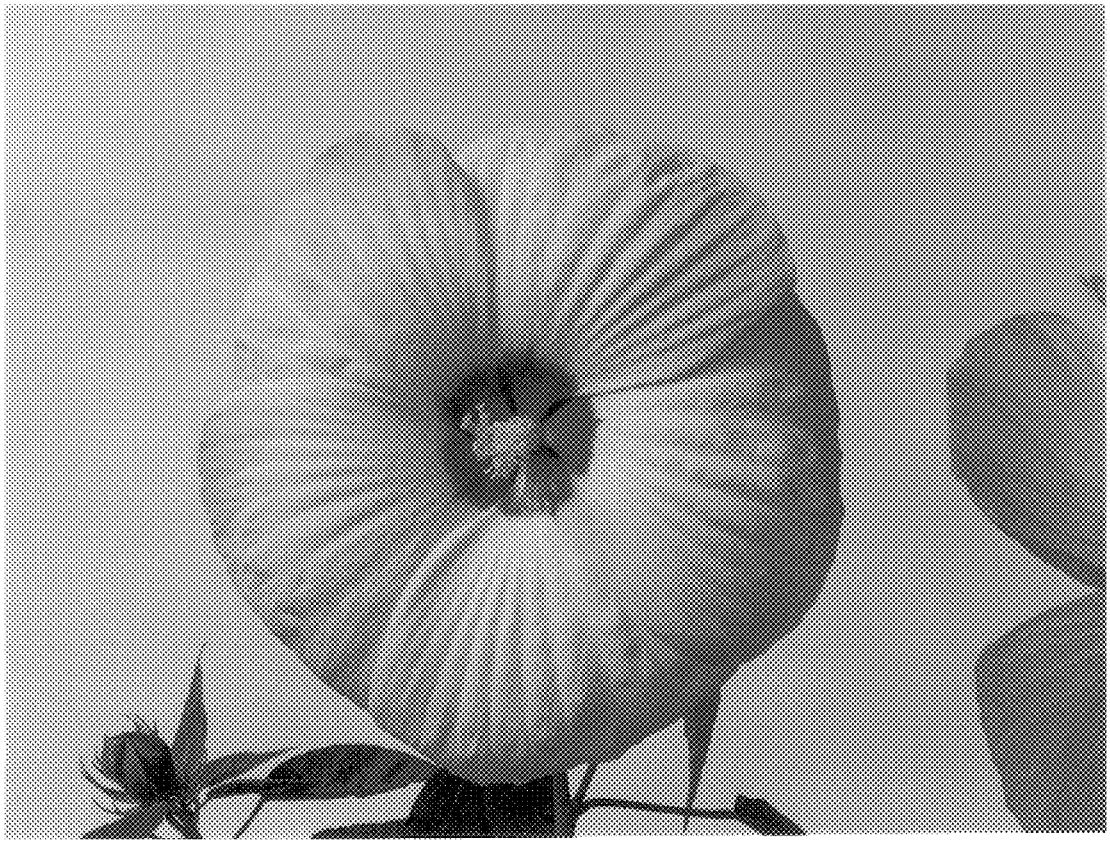
Figure 2:
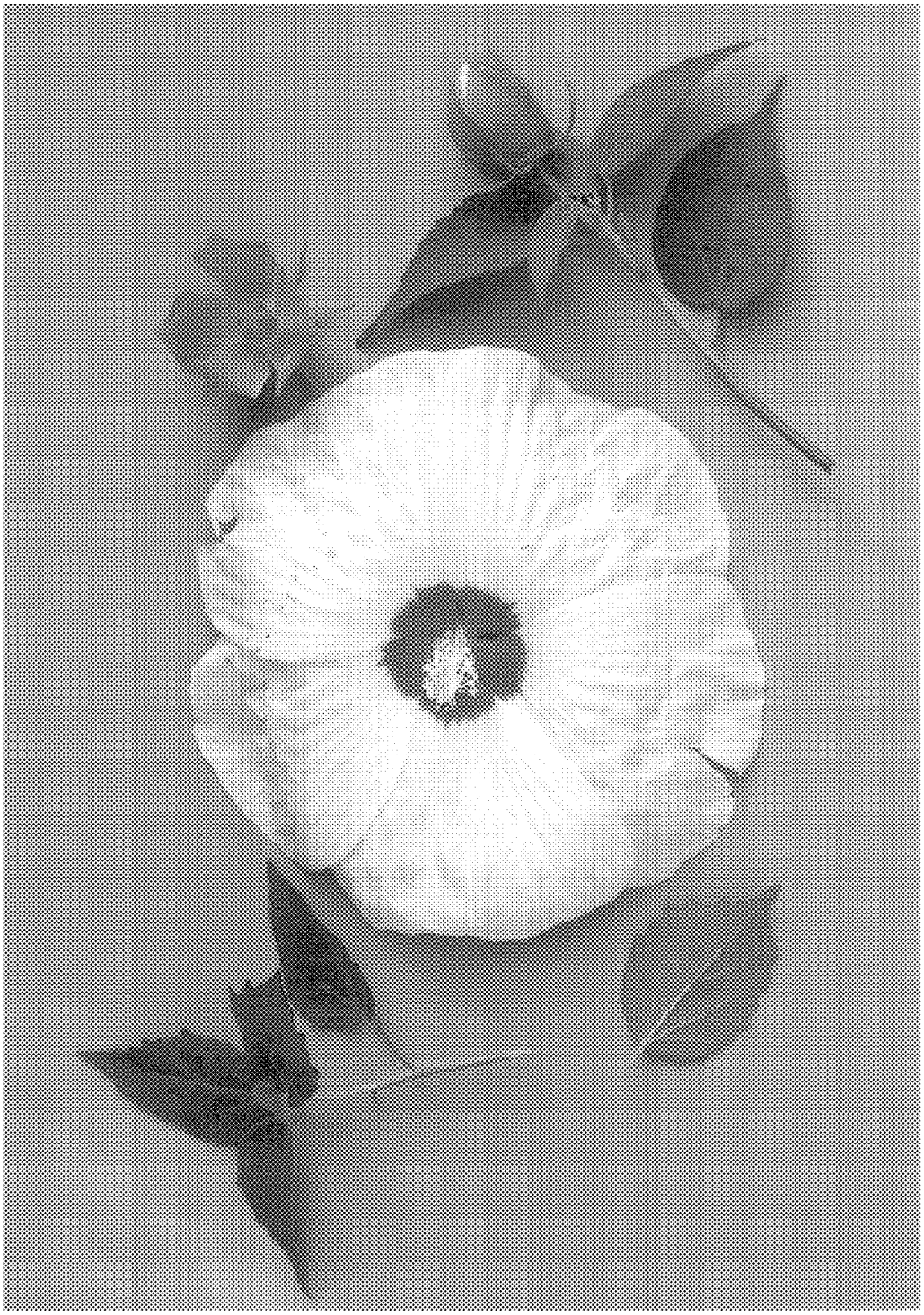
Figure 3:
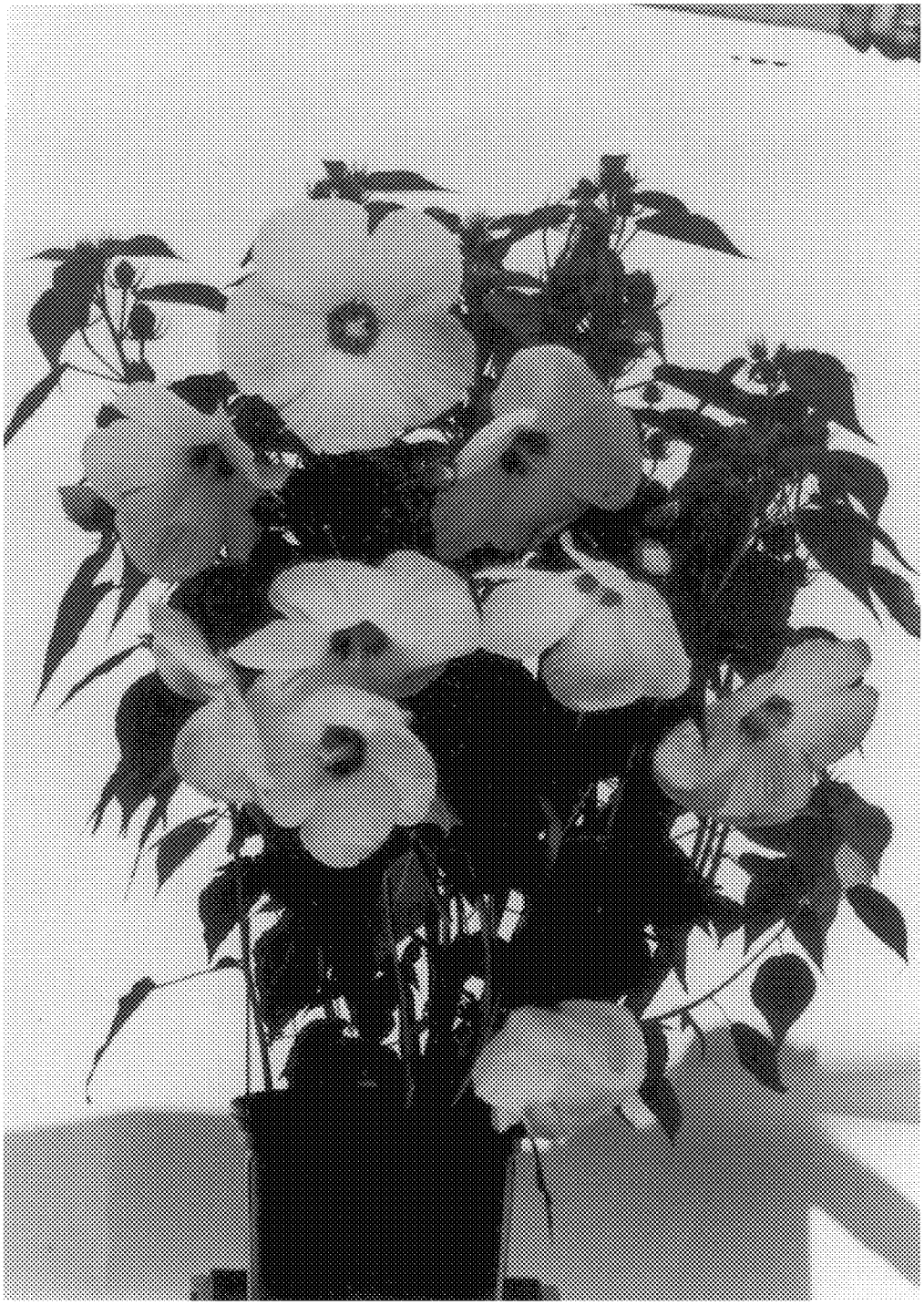

The drawing labeled "FIG. 3" is a view of a potted plant of 'Morrison-Gilberg (VI)'.

DETAILED BOTANICAL DESCRIPTION

Form: Numerous stalks grow upright from perennial roots.

Habit: Individual stalks with many leaves uniformly distributed on the stalk and numerous flowers bloom continuously. Rapid and strong stalk growth have flowers facing outward.

Productivity: Produces continuous new flower displays, vigorous and profuse.

Precocity: Elegant displays of flowers, each stalk displaying one new flower after another. On each stalk, as one flower closes and its petals fall off, a flower next to it and closer to the top of the stalk blooms, so that the displays appear to be continuous. The display periods may vary depending upon climate and the vigor of particular specimens.

Stalks: Mature presentations occur the first year. Strong and smooth skin covered, and hold many leaves and flowers securely. Staking is typically not required under normal full sun growing conditions. However, specimens grown in shaded sunlight produce stalks that are softer and that may require staking. New stalks emerge in May.

Temperature: Winter hardy during freezing winters. On 100 degree (Fahrenheit) days, the flowers bloom equally as they do on a mild day.

Insects and mollusks: Negligible insect damage has occurred to date in any individual plant, even though no pesticides have been used, and no slugs have been observed on the plants.

Animals: Rodents, rabbits and squirrels have not been observed to bother the stalks or roots.

Rooting: The plants root easily without fertilizer and send out their roots quickly and securely.

Foliage: Large leaves evenly distributed vertically and horizontally on the stalks.

Leaves: Abundant and decorative in alternate order. Medium to dark green leaves with margin lengths of from three to eight inches in elongated heart form. Typical leaves are eight inches long by about three and one-half to four and one-half inches wide at the widest part. Top color is Green Group 132B, bottom color is Green Group 132D. Shape is generally cordate, with somewhat irregular crenate margins. Leaf tips are apiculate, bases are cordate, and the venation is pinnate. Texture is matte. Petioles are from two to four and one-half inches. No stipules.

Stems: Green Group 138B.

Petiole color: Lighter green (Green Group 138C) than the leaves.

Height: Mature plants are from three to five and one-half feet in height.

Shape of plant at maturity: Rounded, almost globe-shaped.

THE FLOWERS

Buds: Shaped like a pointed egg and very large one to two days before blooming. White Group 155C. Very large, can be up to four inches in length. A typical bud measures about three and one-half inches in length by about one and three-quarters inches at its widest point Blooming habit: Continuous and free blooming.

Petals: Four and one-half to five and one-half inches long, five per flower.

Diameter of flower: A distinguishing feature of the variety, flowers are from ten to twelve inches in diameter.

Number of flowers: Approximately 12 to 15 flowers per stalk in mature plants, with essentially flat appearance.

Shape: Circular and relatively flat with overlapping petals.

Filament: Each of the approximately 15 filaments attaches to the large style projecting from the center of the flower. Approximately one-eighth to one-quarter inches in length.

Stamens: White Group 155C, three-eighths inch long, very numerous, extending from the style.

Pistil: Three and one-quarter inch long with the stamen and stigma attached. White Group 155D.

Stigma: Five stigma, White Group 155C.

Style: White. Long and supports the stigma.

Pollen: Yellow-White Group 158C.

Shape of petal: Overlapping and broadly obovate (almost reniform), recurves at the base to form a small green star of revealed calyx, with overall circular shape.

Texture: Central one-fourth satiny; outer three-fourths velvety.

Aspect: Like fine kidskin in appearance and strongly self-supporting.

Color: Mostly white, with a pale tinge of pink (Red-Purple Group 69B) on the margins and a deep red eye (Red Group 45A). Eye is two and one-half inch wide. Constant and stable in asexually reproduced plants.

Calyx: Six sepals, one and one-half inch long and one and one-half inch wide, Green Group 139B.

Bractlets: Twelve bractlets, one and one-half inches long and one-quarter inch wide at the base, medium green (Green Group 132C).

Blooming period: Mid summer to frost with continuous color presentation. In suburban St. Louis, the blooming period typically lasts from late July through August. Blooms can occur into October, depending on weather conditions. Container plants produce flowers longer, on lateral stems, as the main stems are cut back and laterals emerge.

Lastingness of the bloom: Individual blooms allowed to remain on the plant last approximately one to three days per bloom.

Peduncle: Two to four inch stiff pedicels, Green Group 132C, to support the flower during blooming and the seed pod formation later.

Fruit: Twelve to sixteen seeds, fruit one inch long and three-quarter inch wide.

Fragrance: Minimal.

Disease resistance: No disease problems have been noted on stalks, leaves or flowers.

Environmental conditions: The plants can stand drought or up to two inches of rainwater without adverse effects.

Winter dormancy: The plants lose their leaves at frost and stems die back to ground level.

Fertility: Midwest topsoil provides adequate nutrients without additional fertilizer.

Regularity of bearing: Consistent year-to-year flowering has been observed.

I claim:

1. A new and distinct variety of *Hibiscus moscheutos* plant, as herein shown and described.

* * * * *